United States Patent [19]

Hess

[11] Patent Number: 5,370,131
[45] Date of Patent: Dec. 6, 1994

[54] CONDOM RESTRAINER RING STRUCTURE WITH RETENTION NOTCH

[76] Inventor: Robert Hess, 804 Moore Dr., Chelsea, Mich. 48118

[21] Appl. No.: 124,943

[22] Filed: Sep. 22, 1993

Related U.S. Application Data

[63] Continuation-in-part of Ser. No. 101,225, Aug. 3, 1993.

[51] Int. Cl.$^5$ ................................................. A61F 6/04
[52] U.S. Cl. ...................................... 128/844; 128/842
[58] Field of Search ............... 24/339, 129 D, 17 AP, 24/543, 17 B, 482; 132/273, 275; 604/353, 349, 351, 347; 128/844, 842, 918; 600/38, 39, 41; 206/69

[56] References Cited

U.S. PATENT DOCUMENTS

| | | |
|---|---|---|
| D. 311,252 | 10/1990 | Pettway . |
| D. 314,827 | 2/1991 | Hendren . |
| 2,257,559 | 9/1941 | Albertson .......................... 24/129 D |
| 2,610,630 | 9/1952 | Crew .................................... 604/347 |
| 3,032,038 | 5/1962 | Swinn .................................. 604/353 |
| 3,626,955 | 12/1971 | Greenwood ......................... 132/273 |
| 4,284,079 | 8/1981 | Adair ................................... 604/349 |
| 4,354,494 | 10/1982 | Hogin . |
| 4,955,392 | 9/1990 | Sorkin . |
| 5,111,831 | 5/1992 | Foggia . |

FOREIGN PATENT DOCUMENTS

| | | | |
|---|---|---|---|
| 2620934 | 3/1989 | France .............................. 128/842 |
| 1252255 | 11/1971 | United Kingdom . |
| 1259284 | 1/1972 | United Kingdom . |
| 2137097 | 10/1984 | United Kingdom ................ 128/844 |

OTHER PUBLICATIONS

Swedish Patent Application #8704797-3 filed on Dec. 1, 1987 by Kurt Wallentin.

*Primary Examiner*—Robert A. Hafer
*Assistant Examiner*—Michael O'Neill
*Attorney, Agent, or Firm*—Dykema Gossett

[57] ABSTRACT

A condom retainer ring structure is for use on a condom that has an elongated thin-walled tubular sheath of resilient material closed at one end and open at the other end, with a bead surrounding the opening. The condom retainer ring structure has a first ring for positioning at the periphery of the opening, adjacent the bead that surrounds the sheath. A second ring is connected to and adjacent the first ring. A bridge having a retention notch therein joins the rings generally in a single plane when the retainer ring structure is not in use and in an unflexed condition. In use, when a condom is worn on the penis of a user, the first ring surrounds the sheath on the shaft of the penis, the second ring encircles the scrotum to anchor the condom, and the bridge is flexed thereby, constricting the retention notch. The retention notch, preferably positioned over the bead of the condom, grabs the bead to retain the condom.

8 Claims, 1 Drawing Sheet

CONDOM RESTRAINER RING STRUCTURE WITH RETENTION NOTCH

REFERENCE TO PRIOR APPLICATION

This is a continuation-in-part of application Ser. No. 08/101,225, filed Aug. 8, 1993.

BACKGROUND OF THE INVENTION

1. Field of the Invention

The present invention pertains to condoms, and more particularly, to a condom retainer ring structure for retaining a condom on the penis of the wearer by using the scrotum of the wearer as anchorage.

2. Description of the Prior Art

Condoms have conventionally been used for birth control, whereby the sperm carrying semen of a male is prevented from entering the uterus of a female as semen is trapped in the condom sheath during sexual intercourse. This method of birth control has not proven fail safe. Condoms are known to slip from the penis during sexual intercourse to allow leakage of the semen into the canal of the female leading to the unfertilized egg. Accordingly, methods have been sought to prevent such slippage and thereby protect against leakage to accomplish the end of birth control.

At present times, condoms have gained more importance because of uses other than for birth control. The proliferation of sexual diseases, particularly AIDS, has brought much concern about the dangers of the semen than with respect to preventing fertilization during sexual intercourse. Studies have shown that the trapped semen of an infected person can prevent the transmission of AIDS during sexual activity. Moreover, use of condoms to prevent AIDS has emphasized the advantages of condoms in protecting against the transmission of other sexual diseases during sexual activity. Accordingly, preventing leakage by preventing the slippage of a condom during sexual activity is an end to be desired.

Several U.S. patents disclose inventions directed to preventing such slippage or otherwise avoiding leakage.

British Patent No. 1,252,255 issued to Kennedy and published Nov. 3, 1971, discloses a condom that has a main body section of general cylindrical shape and circular cross section that is substantially smaller than the head section of the condom. The disclosure teaches of the smaller diameter body section to providing a degree of sealing against the escape of semen that is not ordinarily avoided by conventional condoms of uniform tubular cross section.

U.S. Pat. No. 4,354,494 issued to Hogin on Oct. 19, 1982, discloses a condom for preventing contraception or venereal diseases by including an elongate tubular sheath closed at one end and having a periphery about the opening of the other end to which is secured an elongate resilient retention strap. The retention strap is arranged to encircle the scrotum of the wearer and thereby hold on the sheath. The device uses a conventional bead at the periphery of the opening, and so the strap, which is made of thin rubber, is secured thereto in a fairly weak structure. Accordingly, the strap may readily tear from the condom during particularly active sexual activity. Furthermore, the retention device as taught by Hogin requires a complex manufacture of the condom and the strap which would increase the price of condoms with the possible consequence of decreasing the demand for condoms.

U.S. Pat. No. 5,111,831 issued to Foggia on May 12, 1992, discloses a rollable condom having a retention periphery at its open end. A conventional bead at the periphery of the open end is discontinuous at a notch. A hole is located opposite the notch within the wall of the condom sheath along the bead. The hole has a indentation which is centered on the hole towards the closed end of the sheath. The sheath also has a seal which is located toward the closed end of the sheath to form a circumference of a smaller diameter than the tubular sheath. When the sheath of the condom is fully unrolled onto the penis, the scrotum is positioned through the hole to provide a retention strap around the scrotum. It would appear that without the seal, this device would be easier to manufacture than the device of Hogin. But without the seal, there is even a greater opportunity for semen to leak out of the open end as the bead is not there to provide a seal at the periphery.

U.S. Pat. No. 4,955,392 issued to Sorkin introduces a different solution but with other shortcomings. Sorkin teaches use of a condom that includes a tubular length having a closed first end and an open second end. The open second end includes an integral pubic shield which is adapted to overlay the pubic area of the user. The device does not provide for a seal, although leakage may be lessened by the distance the semen has to travel in order to escape from the condom. According to the teachings of Sorkin, however, the condom is of such a complex structure as to increase its cost, and its coverage may also interfere with the pleasure of the activity when it is in use.

In my earlier filed application, of which this application is a continuation-in-part, I disclosed a combination of a condom and a condom retainer ring structure that has an elongated thin-walled tubular sheath of resilient material closed at one end and open at the other end, with a first ring at the periphery of the open end and a second ring adjacent is attached to and adjacent the first ring, with a bridge joining the rings. In use, the first ring surrounds the sheath worn on the shaft of the penis and the second ring encircles the scrotum to anchor the condom. The disclose acknowledged that the condom retainer ring structure in accordance with the invention may be used with a commercially produced condom. In such a case, the condom is placed on the penis as any commercially produced condom would be placed on the penis and the condom retainer ring structure is placed on the penis and scrotum thereafter.

Although I am quite satisfied with the advantages of the structures disclosed in my earlier filed application, particularly as the advantages relate to the condom having a retaining ring structure built therein, I have conceived of an improvement to the earlier disclosed structures of the condom retainer ring that improves upon its retention, on the shaft of a penis, of commercially produced condoms (those produced without the retaining ring structure being an integral part of the condom), even as my earlier disclosed retaining ring structure improves over the art that proceeded it.

OBJECTS OF THE INVENTION

In view of the above mentioned shortcomings of the prior art designs, it is, as in my earlier filed application, a primary object of the present invention to provide a functional retainer ring structure that retains a condom on the penis during sexual activity.

Another object of the present invention is to provide a condom retainer ring structure that retains a condom on the penis of the wearer and seals the condom at the penis base.

Yet another object of the present invention is to provide a condom retainer ring structure that supports the scrotum to achieve increased stimulation during use.

Still yet another object of the present invention is to provide a condom retainer ring structure that may be used with conventional or standard condoms.

SUMMARY OF THE INVENTION

On a conventional condom, which has an elongate tubular sheath made of a resilient material that is closed at one end and open at the other, a condom retainer ring structure surrounds the sheath adjacent the bead of the condom at the periphery of the opening. The condom retainer ring structure is comprised of two elastic rings that are joined together by a flexible bridge, all disposed generally in a single plane. The bridge has retention notch in it. Preferably, the bridge and two rings are all one integrally molded structure.

Only one of the rings surrounds the sheath at the bead. When used with a commercially produced condom, the condom is placed on the penis, and the condom retainer ring structure is flexed out of the plane in which its component parts are normally disposed, as the condom retainer ring structure is placed on the penis and scrotum. In placing the retainer ring on the penis and scrotum, the retention notch is positioned over the bead so that as the bridge is flexed, the retention notch constricts to grab the bead, thereby retaining the condom with respect to the condom retainer ring structure as the condom ring structure is anchored to the penis and scrotum.

DETAILED DESCRIPTION OF THE PREFERRED EMBODIMENTS

Figure 1:
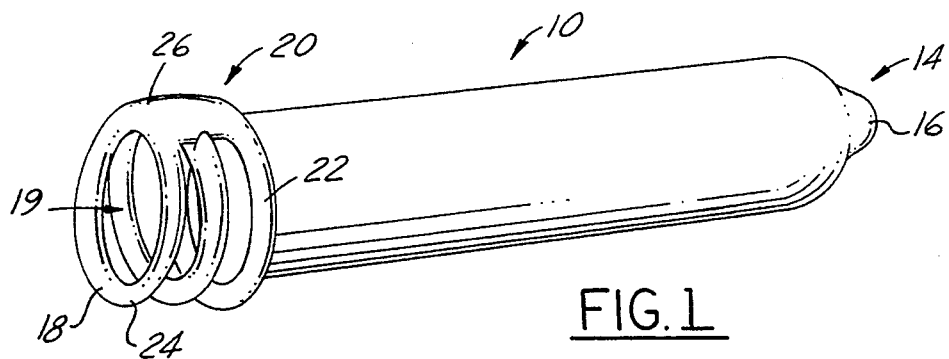
FIG. 1 is a perspective view of a condom retainer ring structure on a condom in accordance with the present invention.
Figure 2:
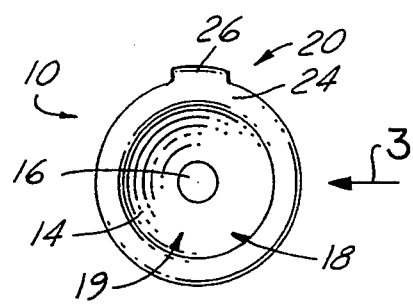
FIG. 2 is a elevational view through the open end of a condom with the condom retainer ring structure positioned thereon.
Figure 3:
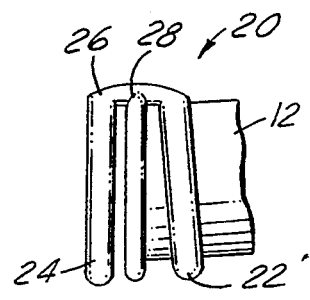
FIG. 3 is a side view of the condom ring structure shown in FIG. 2, generally in the direction of arrow 3 of FIG. 2.

Referring to all of the FIGS. 1-6, a conventional condom 10 comprises an elongate tubular sheath 12 made of a resilient material, such as latex. Sheath 12 is closed at one end 14, which may have a semen receptacle 16 structured thereinto. Sheath 12 has a bead 18 surrounding an opening 19 at an axial end of sheath 12.

A condom retainer ring structure 20, in accordance with the present invention, is positioned on the sheath 12 at the periphery of opening 18. The condom retainer ring structure 20 is comprised of first and second rings 22 and 24, respectively, that are joined together by a bridge 26.

Figure 4:
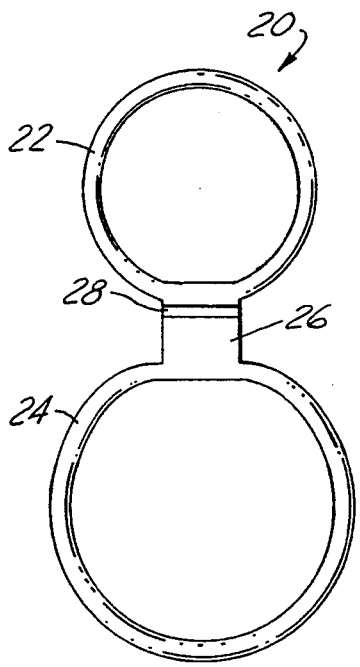
FIG. 4 is an elevational view of a retainer ring structure in an unflexed condition with retainer rings spread apart from one another.
Figure 5:
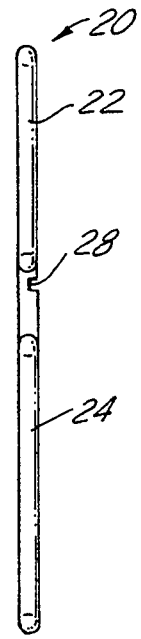
FIG. 5 is an elevational view of the retainer ring structure as shown in FIG. 4.

The first ring 22 surrounds the sheath 12 adjacent the bead 18. It is preferred that, when the condom retainer ring structure 20 is in a relaxed, unflexed state or condition, as shown in FIGS. 4 and 5, the first ring 22, the second ring 24 and the bridge 26 lie adjacent one another generally in a plane. Further, in the preferred embodiment the diameter of ring 22 is generally 27 mm., the diameter of the second ring is generally 50 mm. and the thickness of either ring is generally 4 mm.

The bridge 26 has a retention notch 28 therein disposed generally closer to the first ring 22 than the second ring 24. In the preferred embodiment, the retention notch 28 is about 2 mm. in width and depth. Because the overall structure of the condom ring structure 20 is flexible, when the rings 22 and 24 are flexed with respect to one another as shown in FIGS. 1-3 and 6, the retention notch 28 is constricted, so that if the bead 18 of the condom is positioned under the retention notch 28, the retention notch constricts to grab the bead 28, thereby retaining the bead 18, and condom sheath 12 attached thereto with respect to the condom retainer ring structure 20.

Preferably, the condom retainer ring structure 20 is made of a silicon elastomer molded in a steel compression injection mold. The material content makes the condom retainer ring structure 20 highly elastic and stretchable to be received comfortably over scrotoms of a wide range of sizes and shafts of penises of a range of diameters. Accordingly, the condom retainer ring structure 20 will accomodate most males. The material content also makes the condom retainer ring structure 20 washable and reusable.

Figure 6:
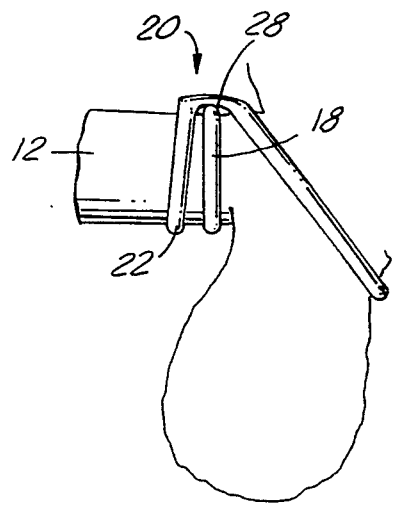
FIG. 6 is a partial side view of the condom retainer ring structure positioned on an erect penis.

To use the condom 10, after it is removed from its packaging, the head of the penis is pressed against closed end 14 from the inside of the condom and the condom is unrolled along the sheath 12 until the condom substantially covers the shaft of the penis. The condom retainer ring structure 20 is placed on the penis and scrotum thereafter. This would be done by flexing the bridge to situate the rings 22 and 24 generally axially adjacent one another and placing both rings 22 and 24 over the head of the penis, preferably, the penis being inserted through ring 24 before ring 22. Both rings are drawn to the base of the shaft of the penis close to or contiguous with the bead of the standard condom 10. The second ring 24 is then manipulated to receive the scrotum therethrough, so that the ring is situated on the penis and scrotum as shown in FIG. 6. The bridge 26 is then unflexed, as by pulling up on the rings supported by the index and middle fingers of one hand and pressing downwardly on the bridge 26 with the thumb. The bead 18 of the condom 10 is then manipulated (with the other hand) to position the bead 18 in the retention notch 28. The bride 26 is released in a flexed state because of the relative positions of the rings 24 and 26, constricting the notch 28 so that it grabs the bead 18. The condom 10, attached by its bead, is retained relatively to the condom retainer ring structure 20, which is itself anchored to the penis shaft and the scrotum.

It should be understood that a condom in accordance with the present invention is particularly suitable for lubricants because the condom retainer ring structure 20 retains the condom better than a conventional lubricated condom, which has a tendency to slip. The resilient material specified is not in all embodiments critical, and any material having similar characteristics for use with or of the condom may be substituted therefor. Any embodiment of the invention that has been described in detail may be subjected to modifications and other embodiments incorporating the inventive features. Accordingly, it is intended that the foregoing disclosure is to be considered as illustrating the principles of the present invention as an example of those features and not as a delimiting description, which is the purpose of the claims that follow.

I claim:

1. A combination of a condom and a condom retainer structure, the combination comprising:

an elongated thin-walled tubular sheath of resilient material being closed at one end and having a bead surrounding an opening at a second end; and a single-piece retainer ring structure including a first ring surrounding said sheath; a second ring adjacent said first ring; and a bridge joining said first ring with said second ring, said bridge including retention means for retaining said retainer ring structure in a fixed position relative to said bead;

wherein said bridge is attached to said bead by said retention means, said retention means grabs said bead, and said retention means is a notch.

2. The combination of claim 1, wherein said notch is constricted when said first ring and said second ring are flexed toward one another.

3. The combination of claim 1, wherein said notch is constricted when said bridge is flexed.

4. A single-piece retainer ring structure for wearing on the penis and scrotum of a male wearer, the structure comprising:

a first ring for encircling the penis;

a second ring adjacent said first ring, said second ring for encircling a scrotum, said retainer ring structure being in a flexed state when said first ring is in a position for encircling said penis and said second ring is in a position for encircling said scrotum;

a bridge joining said first ring with said second ring, said first and second rings and said bridge being integrally formed as a single-piece retainer ring structure and being disposed generally in a plane when said retainer ring structure is in a relaxed state;

wherein said bridge includes retention means carried by said bridge for grabbing a bead defined adjacent an open end on a condom, wherein said retention means is formed in said bridge and wherein said retention means is a notch.

5. The retainer ring structure of claim 4, wherein said notch is constricted when said first ring and said second ring are flexed toward one another.

6. The retainer ring structure of claim 4, wherein said notch is constricted when said bridge is flexed.

7. The retainer ring structure of claim 4, wherein said retainer ring structure is made of a silicone elastomer.

8. The retainer ring structure of claim 7, wherein said retainer ring structure is injection molded.

* * * * *